United States Patent [19]
Uchigaki et al.

[11] Patent Number: 5,270,006
[45] Date of Patent: Dec. 14, 1993

[54] AUTOMATIC SAMPLE ANALYZER

[75] Inventors: Takatoshi Uchigaki, Kyoto; Yasumitsu Takagi, Shiga; Hideki Nishimura, Kyoto, all of Japan

[73] Assignee: Kyoto Daiichi Kagaku Co., Ltd., Kyoto, Japan

[21] Appl. No.: 754,002

[22] Filed: Sep. 3, 1991

[30] Foreign Application Priority Data

Sep. 5, 1990 [JP] Japan .................. 2-236034

[51] Int. Cl.⁵ ............................ G01N 33/00
[52] U.S. Cl. .......................... 422/63; 422/57; 422/65; 422/66; 422/99; 422/104; 221/123; 221/287
[58] Field of Search ............ 422/56, 57, 62, 58, 422/63, 65, 66, 104, 99; 436/808, 810; 435/287, 288, 291, 289, 805, 808; 221/123, 131, 198, 287

[56] References Cited

U.S. PATENT DOCUMENTS

| | | | |
|---|---|---|---|
| 2,216,476 | 10/1940 | Mutz | 221/198 |
| 3,918,910 | 11/1975 | Soya et al. | 422/66 |
| 4,151,931 | 5/1979 | Scherer et al. | 422/57 |
| 4,761,075 | 8/1988 | Matsushita et al. | 356/39 |
| 5,030,418 | 7/1991 | Miyata | 422/63 |

FOREIGN PATENT DOCUMENTS

| | | |
|---|---|---|
| 0006031 | 12/1979 | European Pat. Off. . |
| 0056316 | 7/1982 | European Pat. Off. . |
| 0064691 | 11/1982 | European Pat. Off. . |
| 0180792 | 5/1986 | European Pat. Off. . |
| 0299521 | 1/1989 | European Pat. Off. . |
| 49-77693 | 7/1974 | Japan . |
| 2075263 | 4/1987 | Japan . |
| 3094158 | 4/1988 | Japan . |
| 3101752 | 5/1988 | Japan . |
| 63-252250 | 10/1988 | Japan . |
| 3250564 | 10/1988 | Japan . |
| 85/05563 | 12/1985 | PCT Int'l Appl. . |

Primary Examiner—Michael G. Wityshyn
Assistant Examiner—William H. Beisner

[57] ABSTRACT

An automatic sample analyzer comprising, a plurality of sticks which have a plurality of reagent portions corresponding to different examination items so as to be divided into a plurality of groups of sticks by combinations of the examination items, a plurality of cassettes each having an outlet and a discriminatory mark, the discriminatory mark corresponding to one of the group of the sticks so as to accommodate the one of the group of the sticks, a removal device for automatically taking a desired one of the sticks of the cassettes by using a single removal mechanism.

12 Claims, 7 Drawing Sheets

AUTOMATIC SAMPLE ANALYZER

BACKGROUND OF THE INVENTION

1. Field of the Invention

The present invention relates to an automatic sample analyzer for analyzing urine, blood etc.

2. Description of the Prior Art

Conventionally, various methods are known with respect to measurement of, for example, sugar, protein, or occult blood etc. in urine. In one of the methods, which is widely put to practical use, a plurality of elongated sheetlike sticks each having a plurality of reagent portions are accommodated in a cassette, the sticks are taken out of the cassette one by one such that the reagent portions of each stick are dipped in the sample (urine) and reaction at the reagent portions are subjected to color comparison.

Automatic removal devices for taking the above described sticks out of the cassette are known, for example, from Japanese Patent Laid-Open Publication No. 49-77693, No. 63-252250 etc.

In these devices disclosed in the above publication, a removal mechanism is constructed together with a cassette, therefore only one kind of stick accommodated in a single cassette can be taken out of the cassette by the single removal mechanism.

Meanwhile, there are various combinations of examination items of the sample. Therefore, in an automatic sample analyzer using the above described automatic removal devices, unnecessary items are analyzed in certain cases, thereby resulting in economic loss. To avoid the loss, it can be thought to provide a plurality of cassettes, which accommodate different kind of sticks, corresponding to each combination of examination items, and a plurality of the removal devices corresponding to each cassette. However, in this case, a drawback is that the removal mechanism becomes complicated in its construction and expensive.

SUMMARY OF THE INVENTION

Accordingly, an essential object of the present invention is to provide an automatic sample analyzer in which desired sticks are automatically taken out of a plurality of cassettes by a single removal mechanism, each of said cassettes accommodating a kind of sticks having a plurality of reagent portions corresponding to a combination of examination items such that different kind of sticks are accommodated in different cassettes.

A further object of the present invention is to provide a cassette for the automatic sample analyzer.

In accomplishing these and other objects, according to one embodiment of the invention, there is provided an automatic sample analyzer comprising: a plurality of sticks which have a plurality of reagent portions corresponding to different examination items so as to be divided into a plurality of groups of sticks by combinations of the examination items; a plurality of cassettes each having an outlet and a discriminatory mark, the discriminatory mark corresponding to one of the group of the sticks so as to accommodate the one of said group of the sticks; a removal device for automatically taking a desired one of the sticks out of the cassettes by using a single removal mechanism.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

These and other objects and features of the present invention will become clear from the following description taken in conjunction with the preferred embodiments thereof with reference to the accompanying drawings which are given by way of illustration only, and thus are not limitative of the present invention, and in which:

FIG. 5b is a front view of the cassette shown in FIG. 5a;

FIG. 6 is a bottom view of the cassette shown in FIG. 5a;

FIG. 7 is a front view.

FIG. 9 is a side view.

DETAILED DESCRIPTION OF THE INVENTION

Before the description of the present invention proceeds, it is to be noted that like parts are designated by like reference numerals throughout the accompanying drawings.

Figure 1:
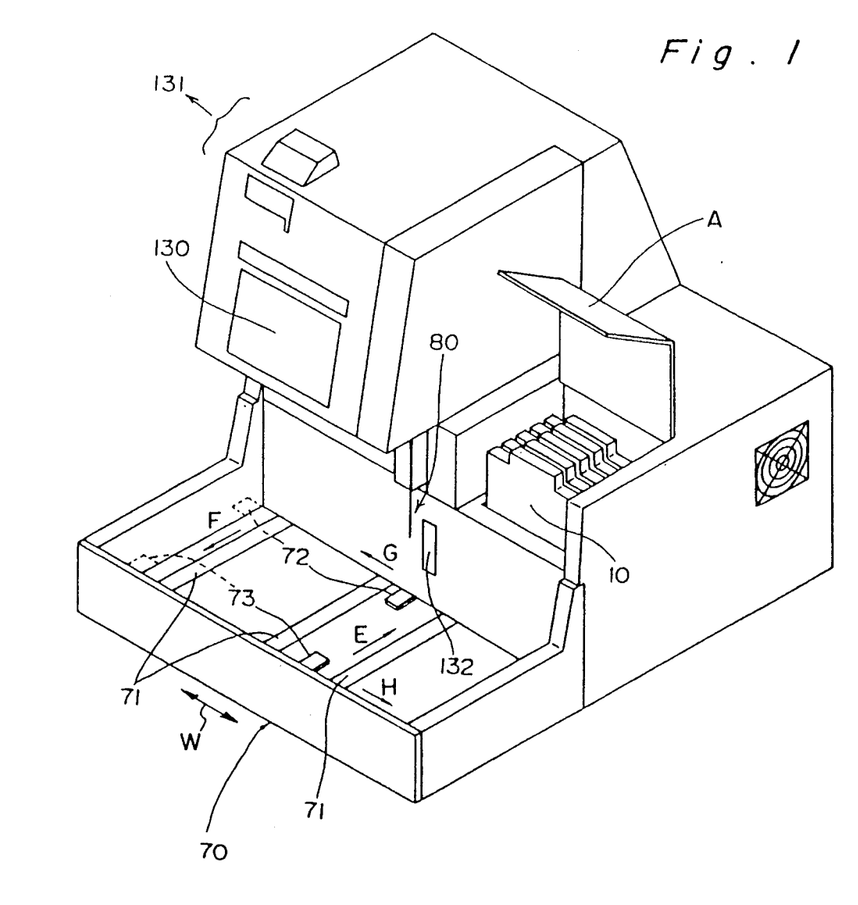
FIG. 1 is a perspective view of an automatic sample analyzer according to the present invention.
Figure 2:
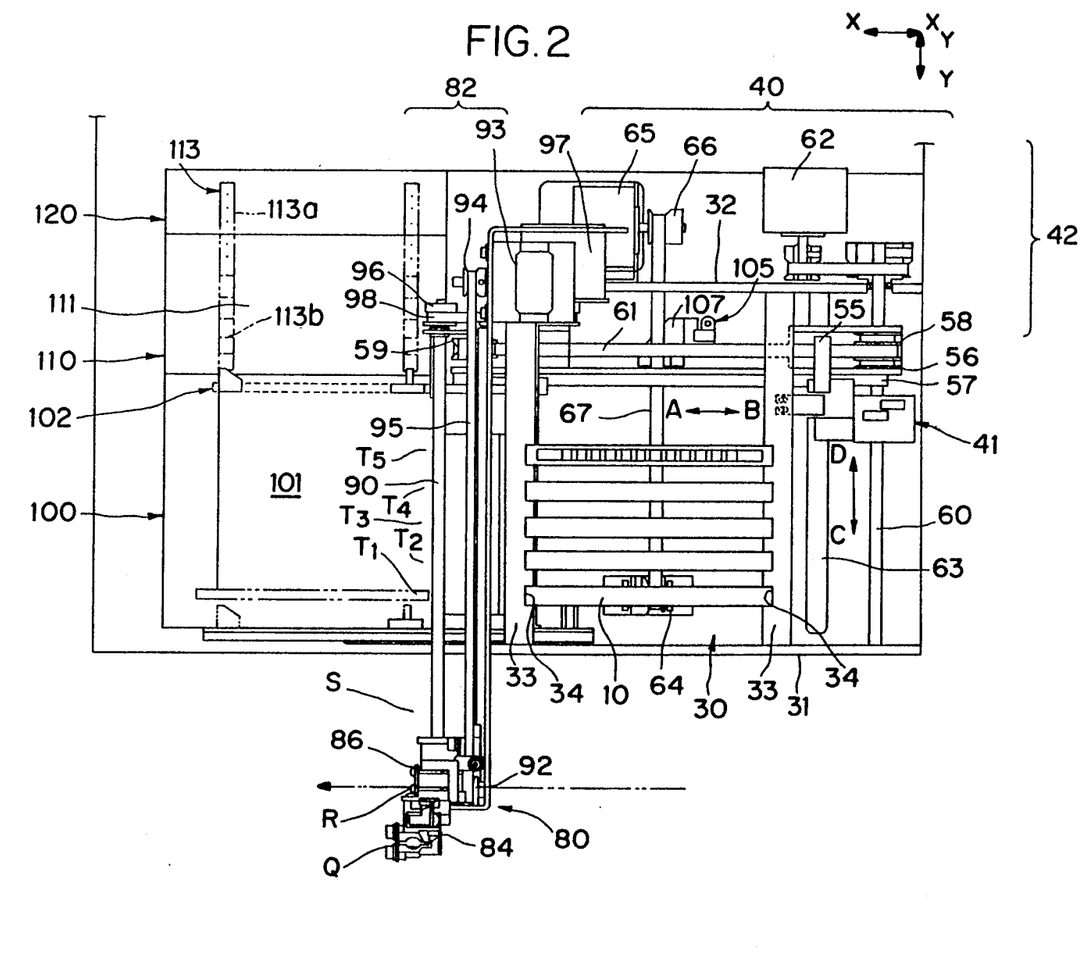
FIGS. 2, 3 and 4 are partial sectional view of the analyzer shown in FIG. 1, FIG. 2 being a plan view, FIG. 3 being a front view and FIG. 4 being a side view.

As shown in FIGS. 1 and 2, the automatic sample analyzer according to the present invention is constituted roughly by a plurality of cassettes 10, a cassette accommodating section 30, a removal device 40, a sample accommodating section 70, a dripping device 80, a base section 100 for taking sticks out of the cassette, a transfer section 110 for accelerating a reaction of the sample on the stick and conveying the stick, and an examination section 120.

Figure 5A:
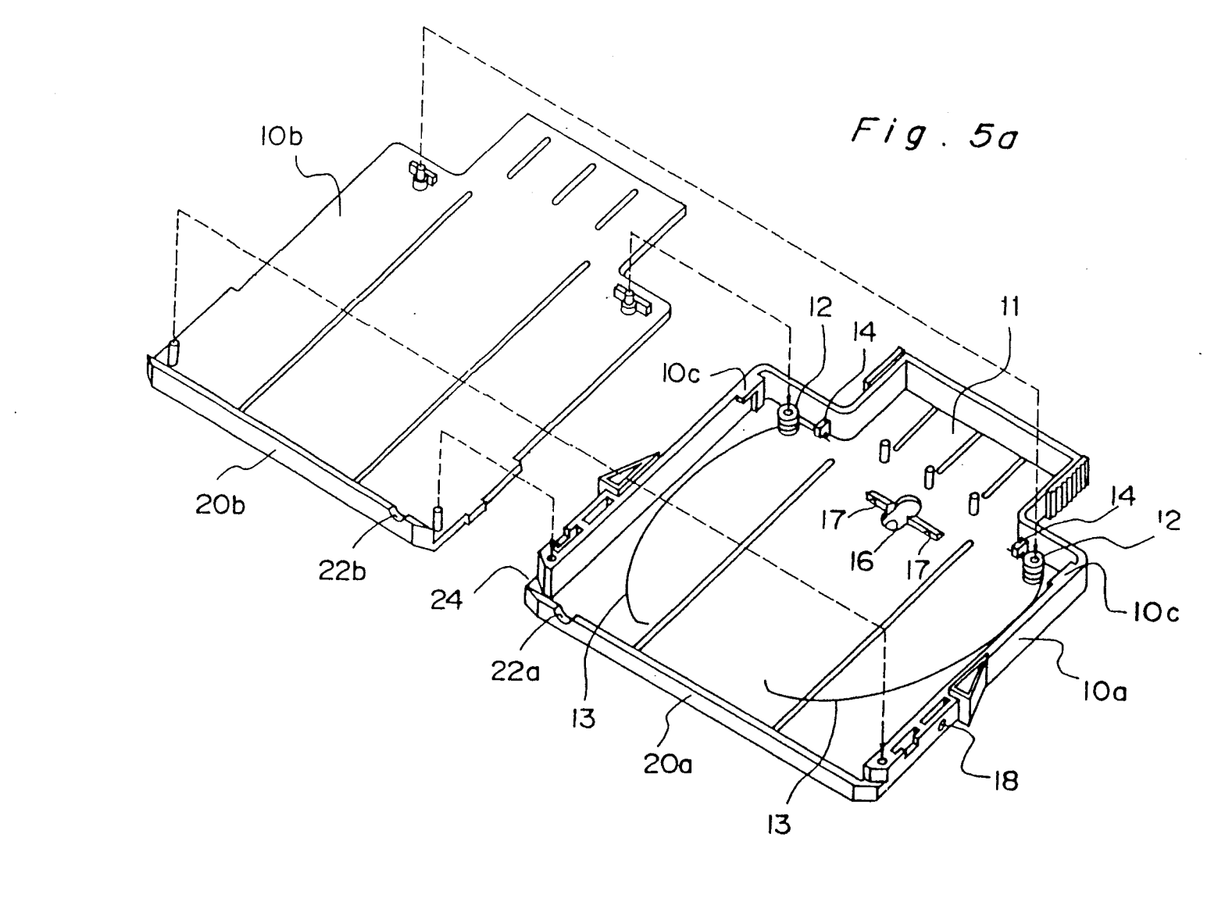
FIG. 5a is an exploded perspective view of a cassette according to the present invention.
Figure 5B:
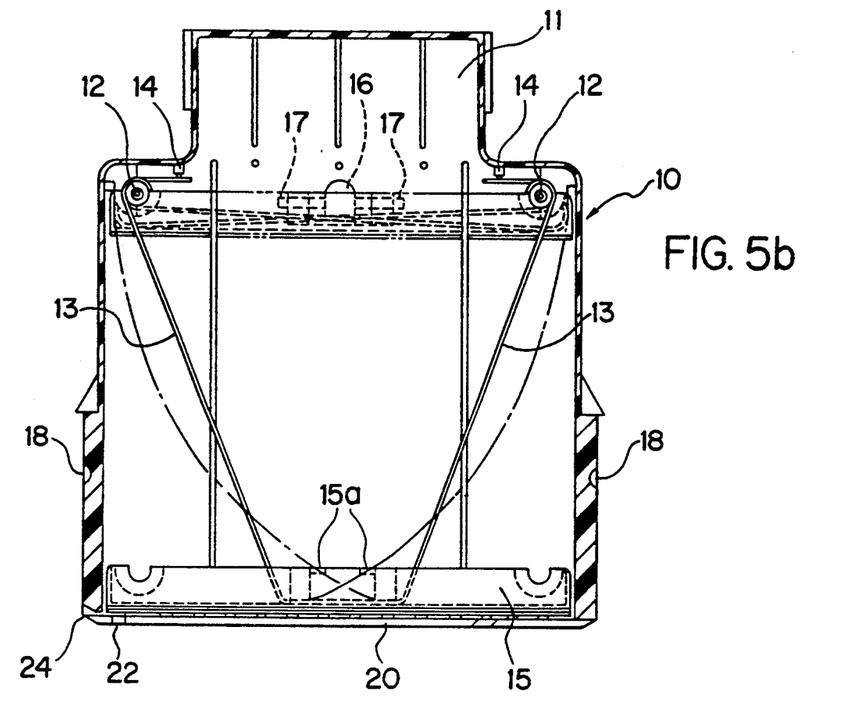
Figure 6:
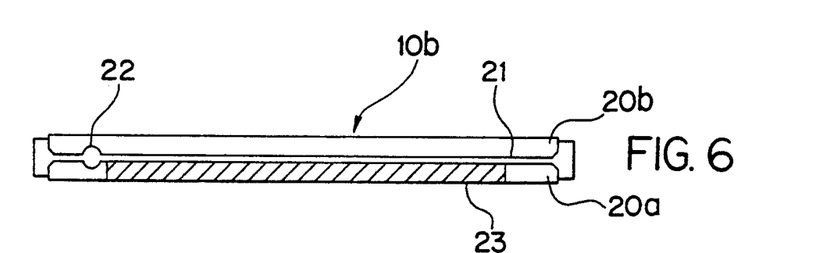

As shown in FIGS. 5a and 5b, the cassette 10 has a form of approximately a rectangular thin parallelepiped by being combined a main casing 10a with a cover casing 10b. In an accommodating room 11 of the cassette 10 projecting upward, a drying agent is accommodated.

As shown in FIG. 5a, a pair of rodlike projections 12 project from upper opposite side portions of the main casing 10a, and a torsion spring 13 is wound around each of the projections 12. One end of the torsion spring 13 is brought into pressing contact with a projection 14 provided adjacent to each of the projections 12 so as to be supported by the projection 14. The other end of the torsion spring 13 is brought into pressing contact with a slide plate 15 which is slidably inserted into the main cassette 10a (See FIG. 5b). Further, vertically extending elongated opening 16 is formed at an upper central portion of the main casing 10a and a pair of protrusions 17 extend symmetrically in opposite lateral direction from a vertically central portion of the elongated opening 16. A pair of engageable portions 10c are formed on inner faces of opposite side walls of the main casing 10a, respectively, while a pair of engageable recesses 18 are, respectively, formed on outer faces of opposite side walls of the main casing 10a. At lower portion of the main casing 10a, a bottom wall 20a is provided such that the bottom wall 20a forms a half of bottom 20 of the cassette 10. There are a plurality of kinds of the sticks 25 classified by combinations of different examination items such that the sticks 25 of the same kind are accommodated in each cassette 10. A discriminatory mark 23 for indicating one of the kind of sticks 25 accommodated in each cassette 10, e.g., a bar code is adhered on the bottom wall 20a of each cassette 10. At one of end portions of the bottom wall 20a, a recess portion 22a is formed, and at opposite end portions, inclined faces are formed.

On the other hand, at the cover casing 10b, a bottom wall 20b is provided facing to the bottom wall 20a of the main casing 10a so as to form a slit 21. And thus, a sensor hole 22 is formed by the recess portion 22b provided at the bottom wall 20b and the recess portion 22a. Further, at a corner of lower portion of the cassette 10 disposed more adjacent to the sensor hole 22 than another corner, an outlet 24 is formed such that a sheet of stick 25 can be passed through the outlet 24. Meanwhile, at the opposite ends of the slit 21, opposed faces are inclined so as to be spaced farther away from each other towards each of the opposite ends of the slits 21.

Figure 7:
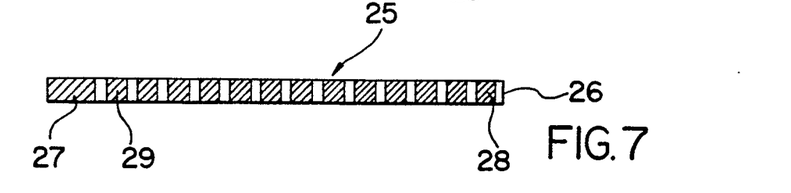
Figure 8:
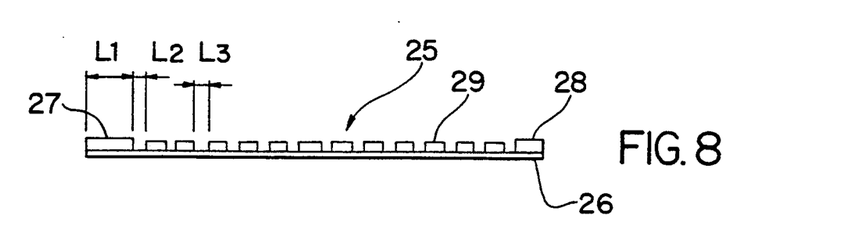
FIG. 8 is a side view of a stick accommodated in the cassette shown in FIG. 5a, respectively.

As shown in FIGS. 7 and 8, the stick 25 is made by adhering a pair of pads 27, 28 and a plurality of reagent portions 29, respectively, on one face of the elongated rectangular sheet 26 such that the pads 27, 28 are situated at opposite ends of the sheet 26, and the reagent portions 29 each corresponding to a different examination item are situated between the pads 27, 28.

As shown in FIG. 8, thickness of the pads 27, 28 are larger than that of each reagent portion 29. Length L1 of the pad 27 disposed more adjacent to the outlet 24 of the cassette 10 than the pad 28 is larger than both a distance L2 between the pad 27 or 28 and a corresponding neighboring one of the reagent portions 29, and a distance L3 between neighboring ones of the reagent portions 29.

Meanwhile, although there may be a case in which a length of a region having no reagent portion becomes larger than the length of the pad 27 depending on the number of the examination items, in this case, it is preferred that a dummy having the same thickness as that of the reagent portion 29 is adhered on a position on which reagent portion is to be adhered.

Although, the above described reagent portion 29 of the stick 25 shown in FIGS. 7 and 8 is made by impregnating reagent into a sheetlike piece, and adhering the piece on the sheet 26, the reagent portion 29 can be made by printing. In this case, the pads 27, 28 become unnecessary.

In advance of loading the stick 25 into the cassette 10, at first a pair of the torsion springs 13 are mounted around the projections 12 of the main casing 10. Thereafter, the slide plate 15 is pressed into the main casing 10a and pushed up against a force of the torsion springs 13 such that the engageable claw 15a provided at central portion of side edge of the slide plate 15 is engaged with the protrusion 17, and the opposite ends of the slide plate 15 is engaged with the engageable portions 10c, whereby the slide plate 15 is prevented from getting out from the main casing 10a, and positioned as shown by two-dot chain line in FIG. 5b. Further, after predetermined number of sticks 25 (e.g., a hundred sticks in this embodiment) of the same kind are mounted in the main casing 10a directing the reagent portion 29 to upward at one time, the cover casing 10b is fit on the main casing 10a, and fixed to the main casing 10a by, for example, hot melting. Finally, the engageable claw 15a of the slide plate 15 is disengaged with the protrusion 17 through the elongated opening 16 such that the sticks 25 are pressed toward the bottom portion 20 by the force of the torsion springs 25.

Figure 3:
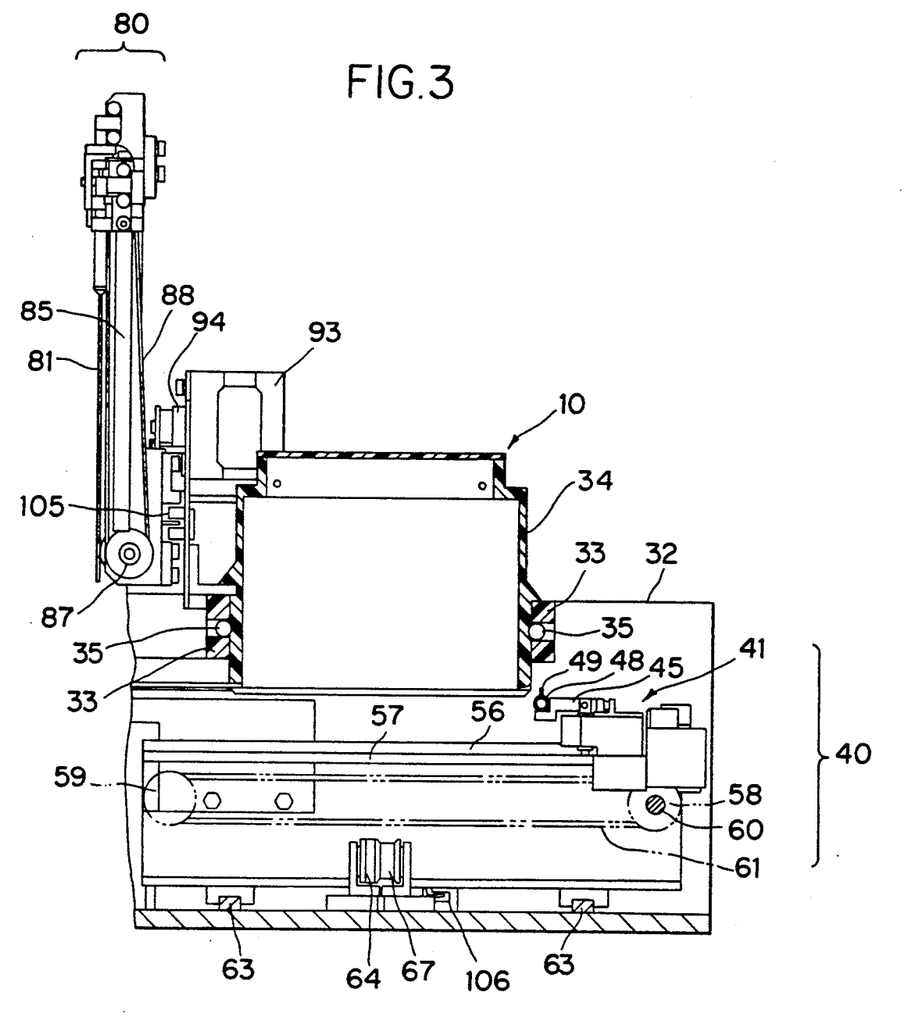

As shown in FIGS. 2 and 3, the cassette accommodating section 30 is constructed by providing five pairs of opposing recess portions 34 for supporting cassettes 10 at predetermined intervals between a pair of support plates 33 disposed between a front plate 31 and a rear plate 32 of the analyzer. In the recess portion 34 of each support plate 33, a ball 35, e.g., plunger-type ball urged towards the recess portion 34, is projected elastically such that the ball 35 is engaged with engageable recess portion 18 of the cassette.

The removal device 40, which is constituted by a base assembly 41 and a drive mechanism 42 for actuating the base assembly 41, is disposed under the cassette accommodating section 30.

Figure 9:
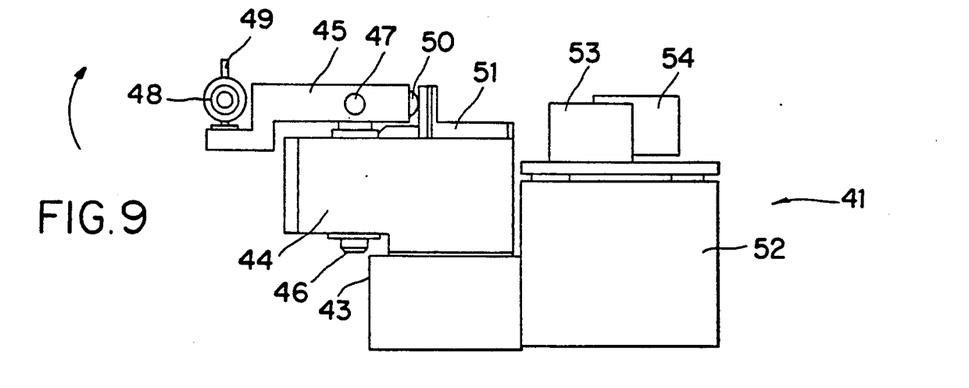
Figure 10:
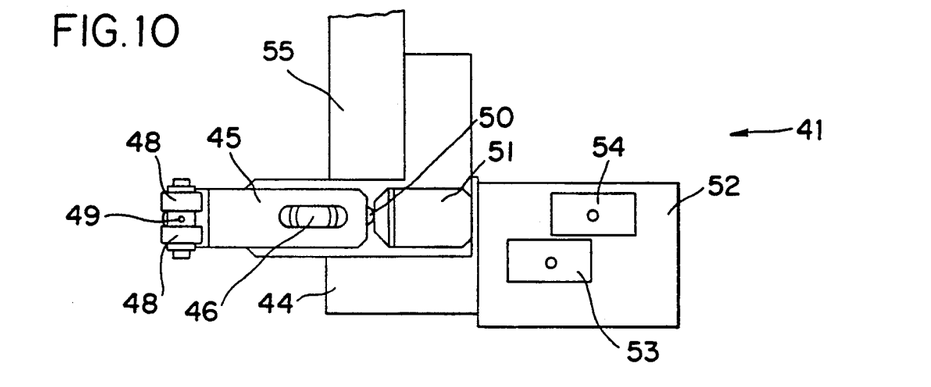
FIG. 10 is a plan view of a removal device used in the analyzer shown in FIG. 1, respectively.

As shown in FIGS. 9 and 10, in one of the example of the base assembly 41, a support table 44 is disposed on a base portion 43, and an arm 45 is provided on an upper face of the support table 44 rotatably about an axis 46, and about an axis 47 by being forced in a direction of an arrow. In a rear end portion of the arm 45, a ball 50 is projected such that rotational movement of the arm 45 is restricted elastically by engaging the ball 50 with a holder 51 standing on the support table 44. At an upper face of the front end portion of the arm 45, a pair of rotatable rollers 48 are provided at predetermined distance. Between these rollers 48, a push pin 49 is projected. To a rear face of the base portion 43, a rear table 52 is coupled. On the rear table 52, a first sensor 53 for identification of the kind of the cassette 10, and a second sensor 54 for detecting of presence or absence of the stick 25 in the cassette 10 are provided so as to deviate from each other in the vertical direction of FIG. 10.

Meanwhile, the base assembly 41, is disposed slidably on a rail portion 57 of a movable frame 56 described below, and fixed through a fixing plate 55 to a belt 61 described below.

The drive mechanism 42 is provided so as to actuate the base assembly 41, as described above. At opposite ends of the movable frame 56, on which the base assembly 41 is disposed slidably, pulleys 58, and 59 are arranged. In FIG. 3, left pulley 59 is provided rotatably, while right pulley 58 is engaged with spline shaft 60 passing through the pulley 59. Over the pulleys 58 and 59, a belt 61 is trained. The base assembly 41 is carried in X—X direction indicated by an arrow(See FIG. 2) by forward and reverse rotation of the motor 62 through the fixing plate 55, the spline shaft 60, the pulley 58 and the belt 61.

The movable frame 56 itself, on which the base assembly 41 is disposed, is provided slidably on a pair of rails 63, and fixed to a belt 67 trained over a pulley 64 provided in front of(under, in FIG. 2) the cassette accommodating section 30, and a pulley 66 mounted around a shaft of the motor 65. The movable frame 56 is carried in Y—Y direction indicated by an arrow (See FIG. 2) through the belt 67 and the spline shaft 66 by forward and reverse rotation of the motor 65. Meanwhile, an interrupting plate 107 provided on lower central portion of the movable frame 56 is detected by a sensor 105, whereby movement of the movable frame 56 is stopped in the direction of an arrow D.

Figure 11:
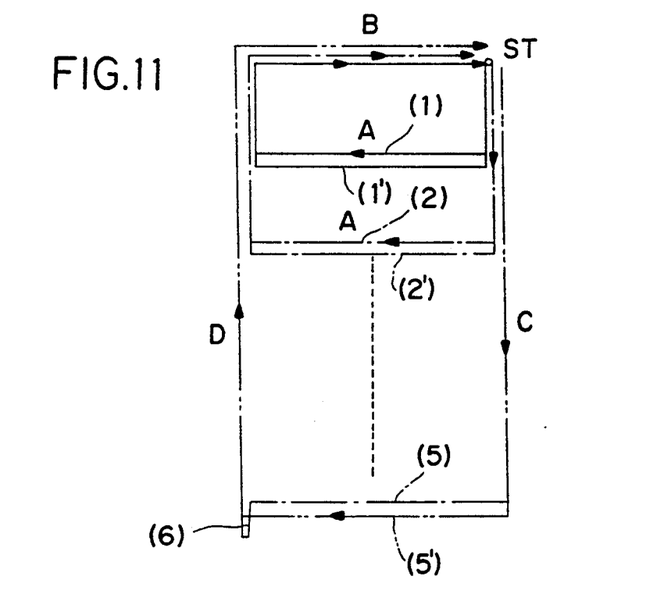
FIG. 11 is a diagram showing a path of a base assembly of the analyzer shown in FIG. 1.

Accordingly, as shown in FIG. 11, the base assembly 41 is carried along a rectangular path from starting position (base point) ST by the drive mechanism 42. Namely, in an operation for reading the discriminatory mark 23 indicating the kind of the cassette 10 described below, the base assembly 41 situated at the starting position ST is carried sequentially from the position of a cassette 10 situated in upper position in FIG. 2 in the cassette accommodating section 30 toward lower portion by rectangular motion (See sequential numerals (1),(2), . . . ,(5) in FIG. 11). Meanwhile, in the operation for reading the discriminatory mark 23, a movement of the base assembly 41 in a direction of an arrow A is performed so as to pass a position in which the first sensor 53 can read the discriminatory mark 23 provided on the lower face of the cassette 10 without the cassette 10 interfering with the push pin 49. Further, as shown by reference numeral (6) in FIG. 11, upon completion of reading of the discriminatory mark 23, the base assembly 41 is slightly carried in the direction of an arrow C and then, is displaced in the direction of an arrow D such that presence or absence of the stick 25 is detected through a sensor hole 22 of each cassette 10 by the second sensor 54.

In an operation for taking the stick 25 out of the cassette 10, the stick 25 is taken out of a cassette 10 having the discriminatory mark 23 corresponding to predetermined combination of the examination items. In this case, the base assembly 41 is carried in the direction of the arrow A along a path (1') or (2') . . . or (5') in FIG. 11 such that the push pin 49 can pass through the slit 21 of the cassette 10.

As shown in FIG. 1, the sample accommodating section 70 is made in a form of upward opening box having rectangular cross section, and provided two pairs of belts 71 at the bottom portion. The belts 71 of each pair are disposed at predetermined distance in a longitudinal direction shown by an arrow W, and driven together. Namely, each pair of the belts 71 is driven in a direction of an arrow E or F by motors which are not shown. Further, at the outside of opposite longitudinal edge portions, first projection pieces 72 and second projection pieces 73 are provided each slidably together and at predetermined distance on the bottom face of the sample accommodating section 70. In the sample accommodating section 70, a plurality of sample racks (not shown) supporting a plurality of standing test tubes each containing a sample are accommodated. The sample racks are conveyed in a direction of an arrow E or F by the belts 71, and conveyed in a direction of an arrow G intermittently by predetermined length so as to make each test tube situate at a dripping position by the first projection pieces 72, and conveyed in a direction of an arrow H by the second projection pieces 73.

The dripping device 80 is constituted by a nozzle 81 and a nozzle carrying mechanism 82.

Upper end of the nozzle 81 is communicated with a suction means and a discharge means (both of them are not shown) so as to suck and drip the sample, and mounted on an nozzle holder 84. The nozzle holder 84 is mounted slidably on a vertical guide 85 standing on a movable table 83 described below, and attached to a belt 88 trained over a pulley 86 provided on upper end of the vertical guide 85, and a pulley 87 engaged with spline shaft 90 described below (See FIG. 4).

Further, the vertical guide 85 is attached to the movable table 83 mounted slidably on horizontal guide 89 extending horizontally. The movable table 83, which is movable together with the pulley 87, is attached to a belt 95 trained over a pulley 92 provided at front portion (right-hand end in FIG. 4) of a side wall 91 projecting from a main body of the sample analyzer, and a pulley 94 mounted on a shaft of a motor 93. A belt 98 is trained over a pulley 96 mounted on one end of the spline shaft 90, and a shaft of a motor 97.

Figure 4:
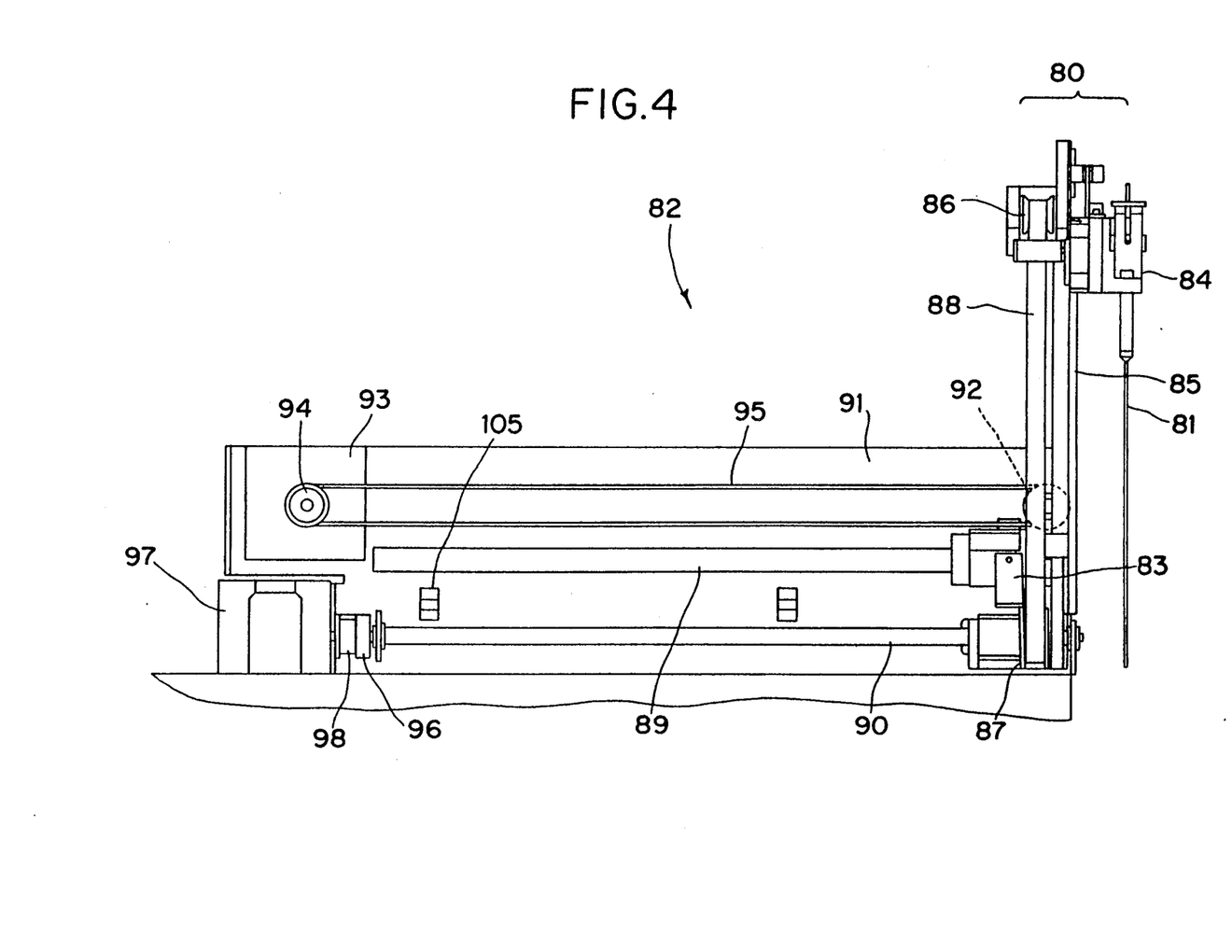

Accordingly, the belt 88 is driven by the spline shaft 90 and then, the nozzle 81 is movable vertically in FIG. 4 such that the nozzle 81 is situated at predetermined position. Further, the belt 95 is driven directly by the motor 93 such that the nozzle 81 is carried through the movable table 83 in a horizontal direction in FIG. 4, and can be situated at each of a interrupting position Q, a sampling position R, a cleaning position S, dripping positions T1, T2, T3, T4 and T5.

The base section 100 for taking the sticks out of the cassette 10 is constituted by a conveying plate 101 and a pair of push claws 102 coupled with each other. The stick 25 in the cassette 10 is pushed out onto the conveying plate 101 by a push pin 49 of the removal device 40, and pushed upward in FIG. 2 at the opposite end portions by the push claws 102. On left-hand push claw 102 in FIG. 2, inclined face is formed such that a stick 25 can be directed to normal direction by the inclined face, even if the stick 25 is pushed out obliquely from the cassette 10. The push claws 102 is coupled to the movable frame 56 of the removal device 40 such that the stick 25 is conveyed to the transfer section 110 with a movement of the base assembly 41 in a direction of an arrow D after dripping the sample to the stick 25 as described below.

The transfer section 110 is constituted by a temperature controlled table 111 and a conveyer 113 provided on the temperature controlled table 111. The conveyer 113 includes a pair of belts 113a which extend in the direction of the arrows C and D, and are juxtaposed at a predetermined distance smaller than the length of the stick 25. A plurality of projections 113b are formed on each of the belts 113a at a predetermined distance substantially equal to the width of the stick 25. The belts 113a are driven intermittently at a predetermined period of 16 sec. in this embodiment so as to transport to an examination section 120, the sticks 25 each having the sample dripped thereon. Further, over the temperature controlled table 111, a temperature controlled plate, which is not shown, is disposed. In the examination section 120, results of reaction between each reagent on the stick 25 and the sample is read such that reaction values corresponding to the results are compared with reference values input beforehand and are analyzed. Thereafter, the results of the examination are printed out by a printer 131.

Meanwhile, reference numeral 130 shows operation panel, and 132 shows reading portion for reading of the barcode the sample.

Upon turning on a power source of the automatic sample analyzer of the above described arrangement, the drive mechanism 42 is actuated so as to cause the base assembly 41 to start the rectangular motion in forward direction of the analyzer (See FIG. 11). Thus, the discriminatory mark 23 of each cassette 10 is read by the first sensor 53, the data concerning the position and the kind of the cassette 10 are stored in a memory unit of a computer which is not shown. Thereafter, the base assembly 41 travels along a left end surface of each cassette 10 such that presence or absence of the stick 25 in the cassette 10 is detected through the sensor hole 22 of each cassette 10 by the second sensor 54, the result of the detection is stored in the memory unit. Namely, the above described operation is performed automatically by turning on the electric power source. Further, the operation is performed also automatically by closing a cover A shown in FIG. 1.

Next, for each sample, the examination items are indicated by bar code or are input by using keys. And then, upon depressing a start button which is not shown, the dripping device 80 is actuated automatically so as to suck the sample by the nozzle 81 when the sample is situated at the sampling position R. Thereafter, the nozzle 81 travels to the cleaning position S, and the sample of required amount for measuring a specific gravity of the sample is discharged and then, the nozzle 81 travels to the dripping position T (T1 or T2 or ... T5). Meanwhile, the dripping position T corresponds to a position of the cassette 10 selected according to a combination of the examination items of the sample.

On the other hand, the drive mechanism 42 is actuated with the motion of the nozzle 81 such that the base assembly 41 is carried in the direction of the arrow C by motor 65 according to a combination of the examination items of the sample, and positioned to right-hand side of the predetermined cassette 10. Further, the base assembly 41 is carried in the direction of the arrow A by the motor 62 such that push pin 49 passes through the slit 21, and pushes out a sheet of stick 25 through the outlet 24 from the cassette 10. At this time, the rollers 48 provided at the end of the base assembly 41 assist the movement of the push pin 49 by rolling on the underside of the cassette 10, and the arm 45 flexes properly so as to compensate for offset in relative position of the slit 21 and the base assembly 41. The stick 25 is pushed continuously until first reagent portion arrives at the dripping position T, thereafter pushed intermittently so as to each reagent portion is situated at the dripping position T sequentially. And thus, very small amount of sample (approximately 5 to 10 μl in this embodiment) is dripped from the nozzle 81 to each reagent portion 29. Upon the completion of all drippings, the stick 25 is wholly pushed out onto the conveying plate 101 by the push pin 49, and pushed to the transfer section 110 by the push claw 102 when the base assembly 41 is returning in the direction of the arrow D. Further, in the transfer section 110, the stick 25 is conveyed for predetermined period of time (approximately one minute in this embodiment) such that a reaction at the each reagent portion is accelerated, and conveyed to the examination section 120 and then, the result of the reaction at the each reagent portion 29 is analyzed by color comparison in the examination section 120.

Meanwhile, when the operation for taking the sticks 25 out of one cassette 10 is performed, the second sensor 54 detects presence or absence of a next stick 25 in this cassette 10, and when the next stick is absent, the second sensor 25 outputs a signal to the memory unit such that a next stick 25 is taken out of another cassette 10 in the next operation, and if another cassette 10 does not exist, a warning is given.

Hereinafter the above described operations are repeated, and the stick 25 corresponding to each sample situated at the sampling position R is suitably taken so as to perform the above described analyze.

When a sample should be examined interruptedly, the nozzle 81 can be carried to the interrupting position Q, and the above described examination can be performed in a same manner by predetermined operation through a operation panel 130. Meanwhile, in the case that the examination is interrupted for example by a stoppage of electric power, the base assembly 41 remains at a position in which the base assembly 41 is situated when the stoppage happens, therefore the analyzer has a function for confirming the position of the base assembly 41.

Further, with respect to the cassette, two or more cassettes 10 of the same kind, each of which accommodates the same kind of sticks, can be provided, whereby when sticks 25 in a cassette 10 are exhausted, a time for exchanging the cassette 10 for new one can be shortened.

Furthermore, in the above described embodiment, urine is used as an example of the sample, however the sample is not confined to urine, but may be blood etc.

As is clear from the above description, in an automatic sample analyzer of the invention, since the cassette is automatically identified, and the stick corresponding to predetermined examination item from the desired cassette, proper examination can be performed.

Further, by providing a pad of predetermined form at the opposite ends of the stick, the removal of the stick from the cassette can be performed smoothly.

Furthermore, since the stick in the cassette is depressed through the slide plate by the torsion spring, the sticks being accommodated in the cassette can be taken out of the cassette with certainty until the last stick.

Furthermore, since an engageable claw is provided on the slide plate, and an engageable member is provided on the upper portion of a side face of the cassette such that the engageable claw is detachably engaged with the engageable member, an operation of the stick can be performed easily.

Although the present invention has been fully described in connection with the preferred embodiments thereof with reference to the accompanying drawings, it is to be noted that various changes and modifications are apparent to those skilled in the art. Such changes and modifications are to be understood as included within the scope of the present invention as defined by the appended claims unless they depart therefrom.

What is claimed is:

1. An automatic sample analyzer comprising:
a plurality of sticks each having a plurality of different reagent portions, the sticks being divided into a plurality of groups of sticks and the groups being for different examination items;
a plurality of cassettes, each cassette having a plurality of said sticks from the same group and each cassette comprising,
a bottom face,
an outlet adjacent the bottom face and a slit defined in the bottom face, said outlet and said slit being configured such that the sticks can be discharged through the outlet by a push pin which travels within the slit,
a slide plate movable between an upper end and the bottom face of the cassette, said sticks being positioned between said slide plate and said bottom face, a torsion spring provided in said cassette, the torsion spring being provided between the upper end of the cassette and the slide plate, the torsion spring urging the slide plate away from the upper end of the cassette, an engageable claw provided on said slide plate, an engageable member provided on an upper portion of a side of said cassette, the engageable claw being detachably engageable with the engageable member to at least temporarily hold the slide plate in a selected position, and a removal device including a single removal mechanism and push pin for taking a desired one of said sticks out of said cassettes by using the single removal mechanism, said pin being movable in a horizontal direction orthogonally to the cassette through the slit in the cassette;

an examining device for analyzing the reagent portions of the sticks;

a conveyor for receiving said desired stick taken out of said cassette by said removal device and for conveying said desired stick to said examining device.

2. The automatic sample analyzer as claimed in claim 1, wherein each of said slits has a predetermined length and a predetermined width, the pin being movable along the length of the slit to remove said sticks one-by-one from the cassette, said sticks each having a generally uniform width and the width of the slit being less than the width of the sticks, the bottom face of the cassette supporting the sticks and preventing deformation thereof.

3. The automatic sample analyzer as claimed in claim 1, wherein each of the sticks has a face on which first and second pads are provided, the first and second pads being provided on opposite ends of the face of the sticks, the plurality of reagent portions being provided between said first and second pads on the face of each stick, the first and second pads having a thickness greater than a thickness of each of the reagent portions.

4. The automatic sample analyzer as claimed in claim 3, wherein the first pad is disposed closer to said outlet than the second pad when the stick is in the cassette, neighboring reagent portions being provided adjacent to the first pad and to the second pad, a length of each pad being defined in a direction between the ends of the stick and the length of the first pad being larger than a distance between said first pad and the neighboring reagent portion and being larger than a distance between the second pad and the neighboring reagent portion.

5. An automatic sample analyzer comprising:

a plurality of sticks each having a plurality of different reagent portions at predetermined positions, the sticks being divided into a plurality of groups;

a plurality of cassettes, each cassette having a plurality of said sticks from the same group and each cassette comprising, a bottom face, an outlet adjacent the bottom face and a slit defined in the bottom face, said outlet and said slit being configured such that the sticks can be discharged through the outlet by a push pin which travels within the slit, a slide plate movable between an upper end and the bottom face of the cassette, said sticks being positioned between said slide plate and said bottom face, a torsion spring provided in said cassette, the torsion spring being provided between the upper end of the cassette and the slide plate, the torsion spring urging the slide plate away from the upper end of the cassette, an engageable claw provided on said slide plate, an engageable member provided on an upper portion of a side of said cassette, the engageable claw being detachably engageable with the engageable member to at least temporarily hold the slide plate in a selected position, and a discriminatory mark disposed on one side of the slit, said discriminatory mark corresponding to one of said groups for said sticks;

a cassette accommodating section accommodating a plurality of said cassettes juxtaposed to each other;

a base assembly including a push pin and a reader, the base assembly being arranged below said cassette accommodating section, the push pin being constructed so as to push individual sticks out of each cassette by traveling along the slits in the cassettes to thereby remove the sticks from the cassettes, the reader being constructed so as to read said discriminatory mark on the cassettes;

a drive mechanism for moving the reader so as to read the discriminatory marks of each cassette in the cassette accommodating section and provide a position of each group of sticks within the cassette accommodating section, and for driving said base assembly in a horizontal direction orthogonally to the cassettes such that said base assembly pushes the sticks one-by-one out of the cassettes; and a dripping section for receiving sticks removed from the cassettes by the base assembly, said dripping section including dripping means for dripping a sample on each of the reagent portions of said sticks received in said dripping section, said sample dripped on each of said reagent portions being examined by color comparison.

6. The automatic sample analyzer as claimed in claim 5, wherein each of said slits has a predetermined length and a predetermined width, the pin being movable along the length of the slit to remove said sticks one-by-one from the cassette, said sticks each having a generally uniform width and the width of the slit being less than the width of the sticks, the bottom face of the cassette supporting the sticks and preventing deformation thereof.

7. The automatic sample analyzer as claimed in claim 5, wherein each of the sticks has a face on which first and second pads are provided, the first and second pads being provided on opposite ends of the face of the sticks, the plurality of reagent portions being provided between said first and second pads on the face of each stick, the first and second pads having a thickness greater than a thickness of each of the reagent portions.

8. The automatic sample analyzer as claimed in claim 7, wherein the first pad is disposed closer to said outlet than the second pad when the stick is in the cassette, neighboring reagent portions being provided adjacent to the first pad and to the second pad, a length of each pad being defined in a direction between the ends of the stick and the length of the first pad being larger than a distance between said first pad and the neighboring reagent portion and being larger than a distance between the second pad and the neighboring reagent portion.

9. A cassette and a plurality of sticks which are accommodated in the cassette comprising:
- a bottom face;
- an outlet adjacent the bottom face and a slit defined in the bottom face, said outlet and said slit being configured such that the sticks can be discharged through the outlet by a push pin which travels within the slit;
- a slide plate movable between an upper end and the bottom face of the cassette, said sticks being positioned between said slide plate and said bottom face;
- a torsion spring provided in said cassette, the torsion spring being provided between the upper end of the cassette and the slide plate, the torsion spring urging the slide plate away from the upper end of the cassette;
- an engageable claw provided on said slide plate; and
- an engageable member provided on an upper portion of a side of said cassette, the engageable claw being detachably engageable with the engageable member to at least temporarily hold the slide plate in a selected position.

10. The cassette and plurality of sticks as claimed in claim 9, wherein each of said slits has a predetermined length and a predetermined width, the pin being movable along the length of the slit to remove said sticks one-by-one from the cassette, said sticks each having a generally uniform width and the width of the slit being less than the width of the sticks, the bottom face of the cassette supporting the sticks and preventing deformation thereof.

11. The cassette and plurality of sticks as claimed in claim 9, wherein each of the sticks has a face on which first and second pads are provided, the first and second pads being provided on opposite ends of the face of the sticks, a plurality of reagent portions being provided between said first and second pads on the face of each stick, the first and second pads having a thickness greater than a thickness of each of the reagent portions.

12. The cassette and plurality of sticks as claimed in claim 11, wherein the first pad is disposed closer to said outlet than the second pad when the stick is in the cassette, neighboring reagent portions being provided adjacent to the first pad and to the second pad, a length of each pad being defined in a direction between the ends of the stick and the length of the first pad being larger than a distance between said first pad and the neighboring reagent portion and being larger than a distance between the second pad and the neighboring reagent portion.

* * * * *